United States Patent
O'Lenick, Jr.

(10) Patent No.: US 7,449,494 B1
(45) Date of Patent: Nov. 11, 2008

(54) POLYMERIC SKIN MOISTURIZING COMPOUNDS

(75) Inventor: Anthony J. O'Lenick, Jr., Dacula, GA (US)

(73) Assignee: SurfaTech Corporation, Dacula, GA (US)

( * ) Notice: Subject to any disclaimer, the term of this patent is extended or adjusted under 35 U.S.C. 154(b) by 838 days.

(21) Appl. No.: 10/958,817

(22) Filed: Oct. 6, 2004

(51) Int. Cl.
*A01N 33/12* (2006.01)
*A61K 31/14* (2006.01)
*A61K 8/00* (2006.01)
*C11D 1/62* (2006.01)
*A61Q 5/02* (2006.01)
*A61Q 1/14* (2006.01)
*A61Q 19/00* (2006.01)
*A61Q 19/10* (2006.01)
*C08G 73/00* (2006.01)

(52) U.S. Cl. .................. 514/642; 424/70.28; 514/847; 510/123; 510/130; 528/422

(58) Field of Classification Search .............. None
See application file for complete search history.

(56) References Cited

U.S. PATENT DOCUMENTS

| | | | | | |
|---|---|---|---|---|---|
| 3,320,215 | A | * | 5/1967 | Conte et al. | 525/420 |
| 4,157,388 | A | * | 6/1979 | Christiansen | 424/70.19 |
| 4,166,894 | A | * | 9/1979 | Schaper | 528/271 |
| 5,318,727 | A | * | 6/1994 | Ohtawa et al. | 510/404 |
| 6,265,364 | B1 | * | 7/2001 | Kilpatrick-Liverman et al. | 510/133 |

FOREIGN PATENT DOCUMENTS

| GB | 2270917 | * | 3/1994 |
|---|---|---|---|
| IN | 177630 | * | 2/1997 |

OTHER PUBLICATIONS

Buriks et. al. Intramolecular Cyclization Products from Alkanolamines and Epichlorohydrin. Journal of Organic Chemistry. 1987, vol. 52, pp. 5247-5254.*

* cited by examiner

*Primary Examiner*—Sharmila Gollamudi Landau
*Assistant Examiner*—Elizabeth S Capan

(57) ABSTRACT

The present invention is directed to a series of new cationic polymeric materials and a process for their use as moisturizing agents on skin. The polymers of the invention are made by the reaction of dimethyl ethanolamine, and tetra 2-hydroxy-alkyl ethylene diamne with di-chloro glycerin in water.

20 Claims, No Drawings

POLYMERIC SKIN MOISTURIZING COMPOUNDS

BACKGROUND OF THE INVENTION

Skin moisturization has been a desired skin benefit for many years. Dry skin can be a result of environmental effects such as sunlight, dry winter air, dermatological condition as well as the application of cleansing materials to the skin such as soap or other harsh detergents which remove oils that are naturally present on the surface of the skin thereby resulting in a loss of moisturization.

U.S. Pat. No. 6,265,364 issued to Kilpatrick-Liverman, et al in Jul. 24, 2001 discloses a composition useful for moisturizing skin. This patent is incorporated herein by reference.

U.S. Pat. No. 6,475,965 also issued Nov. 5, 2002 to Kilpatrick-Liverman, et al describes a skin moisturizing composition comprising a choline salt. This patent is a continuation-in-part of application U.S. Pat. No. 6,265,364. This patent is incorporated herein by reference.

The Kilpatrick-Liverman, et al patents, disclose that choline salt and related compounds are powerful moisturizing agents for skin. Even in a rinse off cleansing composition such material(s) or mixture thereof brings about substantially more moisture on the skin. This can be a statistically significant measurable quantity of moisture on the skin.

The present invention discloses a series of new compounds that are surprisingly more effective than the compounds disclosed in U.S. Pat. No. 6,475,965.

OBJECTIVE OF THE INVENTION

It is the objective of the present invention to provide a new cationic polymeric material which provides outstanding moisturization to the skin and a process foe moisturizing skin which comprises contacting the skin with the novel moisturization agent. Other objectives will become clear in reading the disclosure.

SUMMARY OF THE INVENTION

The present invention is directed to a series of new cationic polymeric materials and a process for their use as moisturizing agents on skin. The compounds of the present invention conform to the following structure:

A—(—B—C—)x—B—A wherein
A is;

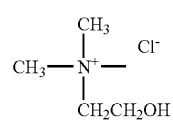

B is;

C is:

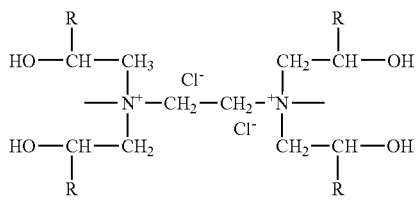

wherein;

R is H or CH₃ x is an integer ranging from 1 to 20.

The compounds of the present invention can be used to moisturize the skin. Significant measurable increases in moisture can be obtained when the composition is applied to the skin. The composition can be in the form of a liquid, solid, or gelled cleansing formulation. The polymeric nature of the products results in an ability to control the penetration of the molecules into the skin and the delivery of moisture to the skin.

The second aspect of the present invention is a process for moisturizing the skin which comprises contacting the skin with an effective moisturizing concentration of a A—(—B—C—)x—B—A wherein;

A is;

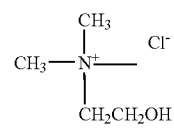

B is;

—CH₂—CH(OH)—CH₂—

C is:

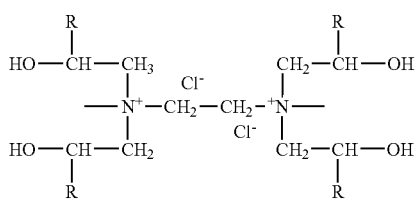

wherein;

x is an integer ranging from 1 to 20;

R is H or CH₃.

The effective moisturizing concentration of the compound ranges from 0.05% to about 15% by weight, with a preferred concentration ranging from 0.1% to 10 wt % by weight.

DETAILED DESCRIPTION OF THE INVENTION

The moisturizing polymer of the present invention is made via the following reaction;

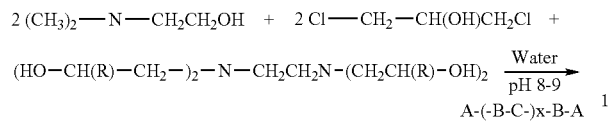

wherein;

A is;

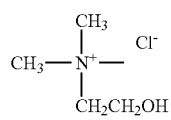

B is;

C is:

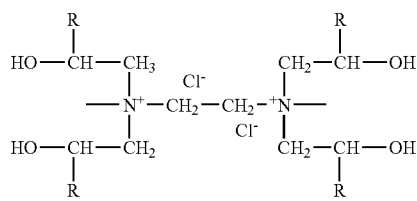

wherein;

R is H or $CH_3$ and x is 1.

The product has a many hydroxyl groups and many cationic nitrogen groups. The hydroxyl containing groups make the product a better moisturizer, and the poly cationic groups make it bind to the skin at anionic groups present thereon.

The moisturizing compound can be formulated into a variety of compositions, liquid, solid and gel-like for delivery of its improved moisturizing benefit. When formulated with a solid, the moisturizing compound can be present with large or small quantities of soap with the remainder of the surfactant being none, smaller or larger quantities of anionic surfactant such as synthetic surfactant. When formulated with a liquid or gel composition, the moisturizing compound is formulated with various amounts of water depending upon the usage of the composition as a cleansing composition, as well as various surfactants of an anionic, nonionic, cationic, amphoteric type, or mixtures thereof. The liquid or gel formulations, particularly the liquids can be formed as a cream or lotion or free flowing liquid which has cleaning abilities, moisturizing and/or conditioning abilities, or a mixture of the cleansing with the moisturizing and/or conditioning benefits. By conditioning is meant increasing the smoothness or suppleness of the skin. By moisturizing is meant the actual increasing of water content of the skin.

Other additional conditioning and moisturizing agents also can be present in the when compounding compositions containing the compounds of the present invention. Typical moisturizing or conditioning materials include urea, lactic acid, pyrrolidone carboxylic acid, amino acids and salts of the acids mentioned.

PREFERRED EMBODIMENT

In a preferred embodiment the effective moisturizing concentration of the compound ranges from 0.05% to about 15% by weight;

In another preferred embodiment the effective moisturizing concentration of the compound ranges from 0.1% to 10 wt % by weight.

In a preferred embodiment x ranges between 1 and 5.
In a preferred embodiment x ranges between 6 and 10.
In a preferred embodiment x ranges between 11 and 20.

EXAMPLES

Raw Materials

Example 1

Dimethyl-Ethanolamine

Dimethyl ethanolamine is n article of commerce, commercially available from a variety of sources. It conforms to the following structure:

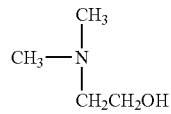

Example 2

1,3-dichloropropan-2-ol 1,3-dichloropropan-2-ol is an article of commerce available from a variety of sources including Phoenix Chemical Somerville N.J. It conforms to the following structure;

Example 3

N,N,N'N'-Tetrakis(2-hydroxyethyl)ethylene diamine

This is an item of commerce commercially available from Synair in Chattanooga Tn. It is made by the reaction of four moles of ethylene oxide with ethylenediamine and conforms to the following structure;

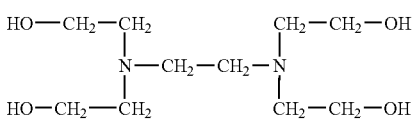

Example 4

Tetrakis(2-hydroxypropyl)ethylene diamine

This is an item of commerce commercially available from Synair in Chattanooga Tn. It is made by the reaction of four moles of propylene oxide with ethylenediamine and conforms to the following structure;

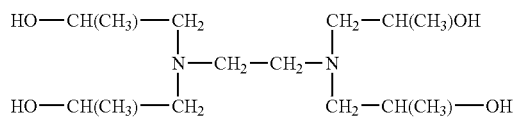

Compound of the Present Invention 1,3-dichloropropan-2-ol is reacted with dimethylethanolamine and Tetrakis(2-hydroxypropyl)ethylene diamine, under aqueous conditions as sown above to give the product of the present invention.

General Procedure

Generally the product is prepared at a concentration of between 70 and 30% by weight. The preferred concentration is 35% Active.

To a suitable reaction flask equipped with agitation, and heat is added the specified number of grams of water. Next add the specified number of grams of dimethyl ethanolamine (DMEA), the specified number of grams 1,3-dichloropropan-2-ol (herein referred to as DCP) and the specified number of grams of Tetrakis(2-hydroxypropyl)ethylene diamine (herein referred to as THEDA). The reaction mass is heated to 80-90° C., and held for 4-8 hours. During that time the % inorganic chloride ion reaches 97% of theoretical. During the reaction time the pH is kept between 8-9. The solution is cooled and used without purification.

EXAMPLES

|  |  |  |  | Diamine | | |
|---|---|---|---|---|---|---|
| Example | Water | DMEA | DCP | Example | Grams | x |
| 5 | 275.0 | 17.0 | 49.0 | 3 | 34.0 | 2 |
| 6 | 275.0 | 11.6 | 50.0 | 3 | 38.4 | 5 |
| 7 | 275.0 | 8.8 | 50.5 | 3 | 40.7 | 7 |
| 8 | 275.0 | 6.4 | 51.0 | 3 | 42.6 | 10 |
| 9 | 275.0 | 3.4 | 51.0 | 3 | 45.6 | 20 |
| 10 | 275.0 | 17.0 | 49.0 | 4 | 34.0 | 2 |
| 11 | 275.0 | 11.6 | 50.0 | 4 | 38.4 | 5 |
| 12 | 275.0 | 8.8 | 50.5 | 4 | 40.7 | 7 |
| 13 | 275.0 | 6.4 | 51.0 | 4 | 42.6 | 10 |
| 14 | 275.0 | 3.4 | 51.0 | 4 | 45.6 | 20 |

Applications

The effect of moisturization can be measured by the appearance of the skin when treated. Untreated skin that is in need of moisturization is rough, scaly and dry looking under the dissection microscope. The application of the moisturization solution to the skin and its effect upon minimizing roughness, scaling and dry appearance is a good measure of moisturization. We performed such an evaluation and rated the performance of a scale of 1 to 5. 1 being poor and 5 being best.

| Sample | Rating |
|---|---|
| Water | 1 |
| 5% Choline | 4 |
| 5% Glycerin | 2 |
| 5% Example 5 | 5 |
| 5% Example 6 | 5 |
| 5% Example 10 | 4 |

The compounds of the present invention is a very effective moisturization agent when applied to rough dry skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polymer which conforms to the following structure:

wherein

A is

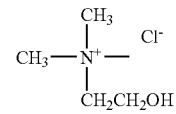

B is

C is

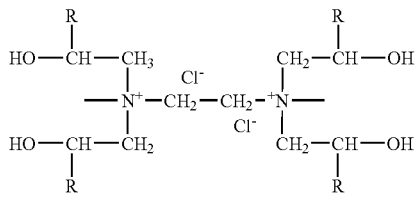

wherein;

x is an integer ranging from 1 to 20.

2. A polymer of claim 1 wherein R is H.

3. A polymer of claim 1 wherein R is $CH_3$.

4. A polymer of claim 2 wherein x ranges between 1 and 5.

5. A polymer of claim 2 wherein x ranges between 6 and 10.

6. A polymer of claim 2 wherein x ranges between 11 and 20.

7. A polymer of claim 3 wherein x ranges between 1 and 5.

8. A polymer of claim 3 wherein x ranges between 6 and 10.

9. A polymer of claim 3 wherein x ranges between 11 and 20.

10. A process for moisturizing skin which comprises contacting the skin with an effective moisturizing concentration of a compound conforming to the following structure;

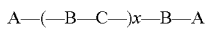

wherein
A is

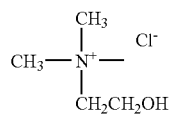

B is

—CH$_2$—CH(OH)—CH$_2$—

C is

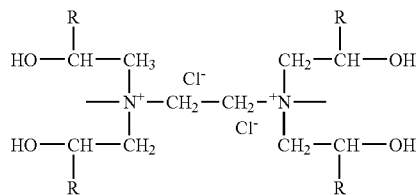

wherein x is an integer ranging from 1 to 20;

R is H or CH$_3$.

11. A process of claim 10 wherein R is H.

12. A process of claim 10 wherein R is CH$_3$.

13. A process of claim 10 wherein said effective moisturizing concentration ranges from 0.05% to about 15% by weight.

14. A process of claim 10 wherein said effective moisturizing concentration ranges from 0.1% to 10 wt % by weight.

15. A process of claim 11 wherein x ranges between 1 and 5.

16. A process of claim 11 wherein x ranges between 6 and 10.

17. A process of claim 11 wherein x ranges between 11 and 20.

18. A process of claim 12 wherein x ranges between 1 and 5.

19. A process of claim 12 wherein x ranges between 6 and 10.

20. A process of claim 12 wherein x ranges between 11 and 20.

* * * * *